(12) United States Patent
Koch et al.

(10) Patent No.: US 9,353,386 B2
(45) Date of Patent: May 31, 2016

(54) MEANS AND METHODS FOR PRODUCING PROPANEDIOL

(75) Inventors: Daniel Koch, Campinas (BR); Guido Meurer, Seeheim-Jugenheim (DE); Jürgen Eck, Bensheim-Auerbach (DE)

(73) Assignee: B.R.A.I.N. Biotechnology Research and Information Network AG, Zwingenberg (DE)

( * ) Notice: Subject to any disclaimer, the term of this patent is extended or adjusted under 35 U.S.C. 154(b) by 0 days.

(21) Appl. No.: 14/125,409

(22) PCT Filed: Jun. 15, 2012

(86) PCT No.: PCT/EP2012/061449
§ 371 (c)(1),
(2), (4) Date: Feb. 14, 2014

(87) PCT Pub. No.: WO2012/172050
PCT Pub. Date: Dec. 20, 2012

(65) Prior Publication Data
US 2014/0178953 A1    Jun. 26, 2014

(30) Foreign Application Priority Data

Jun. 15, 2011 (EP) ..................................... 11004901

(51) Int. Cl.
| | |
|---|---|
| *C12P 7/24* | (2006.01) |
| *C12P 7/18* | (2006.01) |
| *C12N 9/04* | (2006.01) |
| *C12N 9/02* | (2006.01) |
| *C12N 9/10* | (2006.01) |

(52) U.S. Cl.
CPC ... *C12P 7/24* (2013.01); *C12P 7/18* (2013.01); *C12Y 101/01077* (2013.01); *C12Y 102/01* (2013.01); *C12Y 208/03001* (2013.01); *C12N 9/0006* (2013.01); *C12N 9/0008* (2013.01); *C12N 9/13* (2013.01); *Y02P 20/52* (2015.11)

(58) Field of Classification Search
None
See application file for complete search history.

(56) References Cited

U.S. PATENT DOCUMENTS

2010/0330634 A1* 12/2010 Park et al. ................. 435/158

FOREIGN PATENT DOCUMENTS

| WO | 2008119738 | 10/2008 |
|---|---|---|
| WO | 2009031766 | 3/2009 |
| WO | 2009091141 | 7/2009 |
| WO | 2010012604 | 2/2010 |

OTHER PUBLICATIONS

Schweiger et al. FEBS Let. (Jun. 1984) 171 (1) 79-84.*
Selmer T et al. "Propionate CoA-transferase from Clostridium propionicum. Cloning of gene and identification of glutamate 324 at the active site" European Journal of Biochemistry, Blackwell Publishing, Berlin, DE, vol. 269, No. 1, Jan. 1, 2002, pp. 372-380.
International Search Report for International Application No. PCT/EP2012/061449 dated Oct. 9, 2012.
Leal, Nicole A., et al. PduP is a coenzyme-a-acylating propionaldehyde dehydrogenase associated with the polyhedral bodies involved in B12-dependent 1,2-propanediol degradation by *Salmonella enterica* serovar Typhimurium LT2.
Communication pursuant to Article 94(3) EPC received for European Application No. 12729508.7 dated Aug. 7, 2015.

\* cited by examiner

*Primary Examiner* — Nashaat Nashed
(74) *Attorney, Agent, or Firm* — DT Ward, PC; Donna T. Ward; Lingyun Jia (57) ABSTRACT

The present invention relates to a host cell having an elevated expression or activity of an enzyme as compared with the parent cell from which it has been derived, said enzyme having lactoyl-CoA reductase activity. Furthermore, provided is a method of producing lactaldehyde and/or 1,2-propanediol, said method comprising culturing said host cell and/or utilizing said enzyme to produce said compound.

5 Claims, 3 Drawing Sheets

MEANS AND METHODS FOR PRODUCING PROPANEDIOL

CROSS REFERENCE TO RELATED APPLICATIONS

This application is a 35 U.S.C. §371 U.S. National Stage Entry of International Application No. PCT/EP2012/061449 filed Jun. 15, 2012, which claims the benefit of priority of EP Application No.: 11004901.2 filed Jun. 15, 2011, the contents of which are each incorporated herein by reference in its entirety.

REFERENCE TO SEQUENCE LISTING

The present application is being filed along with a Sequence Listing in electronic format. The sequence Listing filed, entitled 20131003SEQLST, was created Dec 6, 2013 and is 11,085 bytes in size. The information in electronic format of the Sequence Listing is incorporated herein by reference in its entirety.

TECHNICAL FIELD

This invention relates to a host cell having an elevated expression or activity of an enzyme as compared with the parent cell from which it has been derived, said enzyme having lactoyl-CoA reductase activity.

BACKGROUND OF THE INVENTION

In this specification, a number of documents including patent applications and manufacturer's manuals are cited. The disclosure of these documents, while not considered relevant for the patentability of the present invention, is herewith incorporated by reference in its entity. More specifically, all the referenced documents are incorporated by reference to the same extent as if each individual document was specifically and individually indicated to be incorporated by reference.

All current biotechnological concepts and methods for the biosynthesis of 1,2-propanediol(PD) utilize the naturally occurring pathway via methylglyoxal which suffers from significant drawbacks as follows: (i) the generation of the highly toxic intermediate methylglyoxal; (ii) reduced efficiency under anaerobic and microaerobic conditions due to higher energetic burden for the cell; and (iii) the fact that it is difficult to achieve optimal control of cell metabolism due to fermentation requirements.

U.S. Pat. No. 6,087,140, WO 1999028481 and U.S. Pat. No. 6,303,352 describe the biosynthesis of PD from sugars with a genetically engineered microorganism expressing a recombinant methylglyoxal synthetase and other enzymatic activities. The described processes utilize the mentioned natural pathway via dihydroxyaceton phosphate and methylglyoxal.

WO 2011012697, WO 2011012702, WO 2011012693, WO 2005073364, US 2007072279, WO 2008116852, WO 2008116853, EP 2192180 and US 2010261239 also propose utilization of the natural PD biosynthesis pathway via dihydroxyaceton phosphate and methylglyoxal, with various modifications to enhance efficacy of this pathway.

WO 2010012604 specifically proposes the utilization of glycerol as carbon source for PD production, in a recombinant microorganism expressing enzymes such as glycerol dehydrogenase (gldA), dihydroxyacetone kinase (dhaK), methylglyoxal synthase (mgsA) or propanediol oxidoreductase (fucO), which are all part of the natural pathway via dihydroxyaceton phosphate and methylglyoxal.

U.S. Pat. No. 7,049,109 describes the utilization of *Klebsiella pneumoniae* to produce PD from sugars. This strain is a natural PD producer, presumably utilizing the methylglyoxal pathway.

Unrelated to current PD biosynthesis pathways, but integral part of the pathway presented in this invention, is an enzyme with lactate CoA-transferase activity, as has been described (Selmer et al., 2002, Eur. J. Biochem. 269: 372-380). The conversion of lactate to lactoyl-CoA through lactate CoA-transferase/propionate CoA-transferase is occurring naturally, more specifically in the pyruvate fermentation pathway found in microorganisms such as *Clostridium propionicum* (Cardon et al., 1947, Archives of Biochemistry & Biophysics 12: 165-171) or *Megasphaera elsdenii* (Baldwin et al., 1965, Biochim Biophys Acta 97: 202-13). There, lactate is converted via lactoyl-CoA and acrylyl-CoA to propanoyl-CoA and finally to propionate, the end product.

In view of the deficiencies of the processes described in the art, the technical problem underlying the present invention can be seen in the provision of alternative or improved means and methods for producing propanediol and compounds related thereto.

SUMMARY OF THE INVENTION

This problem has been solved by the subject-matter of the claims.

DETAILED DESCRIPTION

Figure 1:
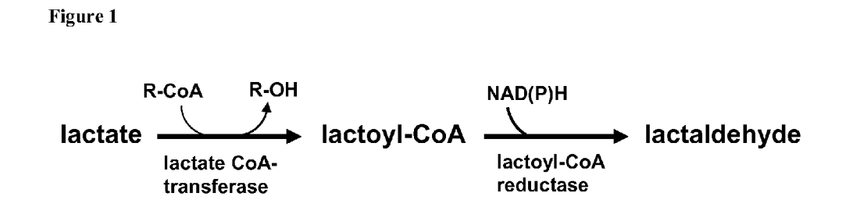
FIG. 1: Scheme of the enzymatic reduction of lactate to lactaldehyde via lactoyl-CoA.

Accordingly, in a first aspect, the present invention relates to a host cell having an elevated expression or activity of at least two enzymes as compared with the parent cell from which it has been derived, said enzymes being (a) an enzyme having lactoyl-CoA reductase activity; and (b) (i) lactate CoA-transferase, and/or (ii) lactaldehyde reductase. The lactoyl-CoA reductase activity mentioned throughout this invention is such as depicted in FIG. 1, where the CoA-bound acid group is reduced to an aldehyde group. This is not to be mistaken with an acid-CoA reductase which reduces other parts than the acid group of the molecule, for instance acrylyl-CoA reductase, reducing the unsaturated acrylyl-CoA to the saturated propanoyl-CoA.

Embodiments falling under the first aspect include: A host cell having an elevated expression or activity compared with the parent cell from which it has been derived, said enzymes being an enzyme having lactoyl-CoA reductase activity and lactate CoA-transferase; and a host cell having an elevated expression or activity compared with the parent cell from which it has been derived, said enzymes being an enzyme having lactoyl-CoA reductase activity and lactaldehyde reductase.

The host cell may be any cell. Preferred host cells are further detailed below. It is understood that preferably the host cell according to the invention is not within the context of animal or human. Accordingly, it is preferred that the host cell is in vitro, in culture, and/or isolated. Also, the host cell may be a unicellular microorganism of eukaryotic or prokaryotic origin. While human stem cell lines are at a skilled person's disposal, it is noted that, to the extent human cells are envisaged, said cells have not been obtained by using or destructing a human embryo. Related thereto, non-human host cells are preferred.

The host cell is derived from a parent cell. The host cell according to the invention differs from said parent cell at least in that, preferably only in that, it has elevated expression or activity of the enzymes as required or recited in the main embodiment or in further embodiments detailed below. Said elevated expression or activity is achieved by, for example, engineering the parent cell with (a) nucleic acid(s) encoding the recited enzyme(s), which engineering with (a) nucleic acid(s) is the subject of a further aspect of the present invention as described below. As an alternative to being engineered with such nucleic acid(s), the host cell may be recombinant in other respects, for example, by being engineered with (a) nucleic acid(s) which enhance(s) or encode(s) (a) polypeptide(s) enhancing the expression or activity of said enzyme(s). A further envisaged means of enhancing expression or activity of said enzymes is a stimulus, preferred examples of said stimulus being compounds such as non-nucleic acid compounds or small (molecular weight preferably below 1000 or 500 Dalton) organic molecules, said compounds being added to and/or taken up by said parent cell. Further envisaged stimuli are changes of the temperature, pH or pressure. By providing said stimulus, the host cell according to the invention is obtained from said parent cell. Accordingly, while this is preferred, it is not required that host cell and parent cell are genetically different.

The present invention provides a lactoyl-CoA reductase, or, in more general terms, an enzyme having lactoyl-CoA reductase activity. In other words, for the purpose of the present invention, either a novel lactoyl-CoA reductase may be utilised, or a previously known enzyme, said previously known being characterized in that it exhibits—possibly so far not recognized—lactoyl-CoA reductase activity. Whether or not a given enzyme exhibits said activity, can be assessed by a skilled person, when provided with the teaching of the present invention, without further ado. For example, lactoyl-CoA may be provided to a test host cell expressing a candidate enzyme, and the formation of lactaldehyde or any downstream product thereof, such as 1,2-propanediol, is monitored. In case lactaldehyde and/or any of the downstream products is being formed, this is indicative of said candidate enzyme being an enzyme having lactoyl-CoA reductase activity. It is understood that the parent cell, characterized in that said nucleic acid is absent, does not produce lactaldehyde or 1,2-propanediol, or to a lesser extent, as compared to a test host cell comprising a nucleic acid, said nucleic acid encoding an enzyme with lactoyl-CoA reductase activity. Preferred enzymes having lactoyl-CoA reductase activity can be found within the group of succinyl-CoA reductases, malonyl-CoA reductases, butyryl-CoA reductases, propionyl-CoA reductases and acetyl-CoA reductases. We furthermore refer to Example 1 providing evidence of lactoyl-CoA reductase activity.

The term "recombinant" has its meaning as established in the art. It refers to the presence of genetic material in the host cell which is not present in the parent cell. The genetic material absent from the parent cell may be a nucleic acid encoding an enzyme according to the invention. Alternatively or in addition, it may be the sequence of a vector which renders the host cell different from the parent host cell. More specifically, a nucleic acid encoding an enzyme, the nucleic acid as such being present in the parent cell, may be placed in a different context within a vector, the presence of such a vector rendering the cell different from the parent cell. Vectors according to the invention are discussed in more detail below.

It is understood that the term "elevated" refers to a statistically significant difference in expression or activity. In preferred embodiments, expression and/or activity are elevated at least 1.5-fold, 2-fold, 3-fold, 4-fold, 5-fold, 10-fold, 20-fold, 50-fold, 100-fold, 1000-fold higher or above as compared to the expression and/or activity of the enzyme under consideration in the parent cell. Also the case where the parent cell has no expression of one or more of the recited enzymes is embraced. In the latter case, and also in general, it is preferred that the host cell has an expression or activity of the recited enzymes which provides for a production of lactaldehyde or propanediol, when provided with (a) carbon source(s) as further detailed below, of at least 100 mg/L culture.

The term "expression" is understood to refer to the expression level of the mRNA encoding the respective enzyme on the one hand and protein expression level of the enzyme on the other hand. Means and methods for determining the mRNA expression levels are well-known in the art as are means and methods for determining protein expression levels. Such means include Northern-blotting, quantitative PCR, hybridization to microarrays or DNA chips on the one hand and Western-blotting, immunoassays and protein arrays on the other hand.

Figure 2:
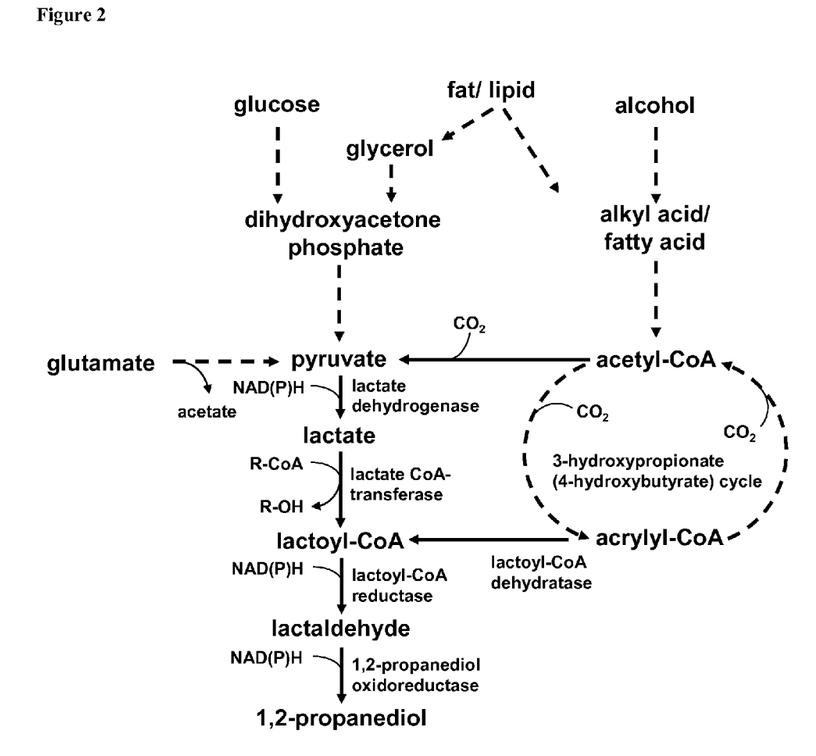
FIG. 2: New pathway for the biosynthesis of 1,2-propanediol utilizing the intermediate lactoyl-CoA. It also provides an overview of preferred carbon sources and their known degradation pathways abbreviated by dotted arrows.

An enzyme having lactoyl-CoA reductase activity is the key enzyme in the pathway for the production of propanediol according to the invention, said pathway being displayed in FIG. 1 and, in a broader context, FIG. 2 as enclosed herewith.

The host cell according to the invention is a means for the biotechnological production of 1,2-propanediol (propylene glycol) from various carbon sources by a novel and not naturally occurring biosynthetic pathway, wherein lactoyl-CoA is a key intermediate in said pathway, lactoyl-CoA being a substrate for lactoyl-CoA reductase.

As compared to the prior art reviewed above, the new pathway according to the invention avoids the toxic intermediate methylglyoxal and utilises the naturally occurring strong carbon flux to lactate. In other words, lactate is formed to a significant degree in virtually most of the naturally occurring cells. The pathway according to the present invention which pathway may be realised with the host cells according to the invention, is furthermore characterised by an energetic advantage over the methylglyoxal pathway. This is explained in more detail in the following.

Especially under the anaerob conditions necessary or beneficial for the efficient fermentative production of a reduced product (here PD) from a more oxidized substrate (like glycerol or glucose), maintaining redox balance and a positive energy balance (necessary for cell maintenance or viability) is critical. Anaerob conditions lead to a high intracellular NAD(P)H concentration, as well as microaerob conditions (such as conditions with very limited access of the cell to oxygen, for example with dissolved oxygen ≤10 µM), since the redox equivalents which accumulate during energy and building block generation cannot or cannot completely be converted to ATP through reduction of oxygen to water. Thus, all enzymatic reactions requiring NAD(P)H as co-factor are enhanced and the metabolism is pushed towards the generation of the reduced product PD, which can be regarded as a "waste stream" to regenerate NAD(P)+.

A PD biosynthetic process using the lactoyl-CoA pathway according to the present invention and fulfilling the above demands can be broken down into the following reaction equations:

1 glycerol->acetyl-CoA+formate+1 ATP+2 NADH 1 glycerol+acetyl-CoA->PD+acetate+1 ATP−1 NADH 1 glycerol->PD−1 ATP−1 NADH, with 1 acetate+2 ATP->1 acetyl-CoA summary: 3 glycerol->2 PD+formate+acetate+1 ATP

According to this formula, the maximum yield would be 0.55 g/g (PD/glycerol) for the lactoyl-CoA based pathway according to the invention, with a surplus energy of 0.33 ATP per glycerol molecule.

For comparison, a breakdown of the methylglyoxal pathway is as follows:

1 glycerol->acetate+formate+2 ATP+2 NADH 2 glycerol->2 PD–2 ATP–2 NADH 1 glycerol->ethanol+formate+1 ATP summary: 4 glycerol->2 PD+acetate+formate+ethanol+1 ATP According to this formula, the maximum yield would be 0.41 g/g (PD/glycerol) for the methylglyoxal pathway, with a surplus energy of 0.25 ATP per glycerol molecule. Without the degradation of one additional glycerol molecule to ethanol for the benefit of one redox neutral ATP, the total reaction would be redox and energy neutral. Such a reaction would typically not occur in a living cell, since the host cell requires a surplus ATP for metabolic maintenance.

According to the stated reactions, under realistic anaerob conditions, the lactoyl-CoA based pathway could produce approximately 34% more PD than the common methylglyoxal based pathway and in addition 33% more ATP, depending on actual maintenance requirements.

The enhanced productivity stems mainly from the more efficient use of acetyl-CoA. In the lactoyl-CoA pathway, the generated acetyl-CoA can be used for a CoA-transfer reaction, saving 2 ATP otherwise necessary to activate an acid to yield an acid-CoA. In contrast, in the methylglyoxal pathway, acetyl-CoA is converted to acetate, yielding only one ATP, or to ethanol for $NAD^+$ regeneration, yielding no ATP. Thus, under anaerob and microaerob conditions, the lactoyl-CoA pathway is superior to the methylglyoxal pathway in terms of energy generation, which translates into a significantly enhanced productivity potential. This energetic advantage may decrease only under fully aerob conditions, where the full energy content of each acetyl-CoA can be harnessed through the citric acid cycle and ATP generation with oxygen and reducing equivalents. However, aerob conditions are preferably avoided, noting that they may be disadvantageous for the fermentative production of the reduced PD in other aspects (such as low NADH concentration, detrimental regulation or unwanted biomass production). Accordingly, preferred conditions for the methods and uses disclosed below are anaerob or microaerob conditions, the term "microaerob" being defined above.

In the light of the necessary redox neutrality and energy availability, the main fermentation pathways to ethanol or acetate can be completely eliminated when using the new PD pathway, as detailed in the previous paragraph and the enclosed example. This is in contrast to the methylglyoxal pathway, which requires additional fermentation products like acetate or ethanol to accomplish redox neutrality and energy availability. Thus, a more strict control of the metabolism is possible for the new PD pathway as compared to the methylglyoxal pathway. This is expected to greatly enhance productivity of the pathway according to the invention while reducing the necessity for complicated fine tuning of fermentation pathways in order to optimize carbon flux towards the desired product.

In summary, the new PD pathway has several advantages over the methylglyoxal pathway:
(i) no highly toxic intermediate methylglyoxal,
(ii) strong carbon flux from various carbon sources to the intermediate lactate in natural or engineered hosts,
(iii) higher energy efficiency under anaerobic and microaerobic conditions, and
(iv) more stringent control of metabolism due to reduced fermentation requirements.

Preferably, said host cell according to the invention has elevated expression or activity of all three enzymes as defined in the first aspect of the invention.

As is apparent from FIG. 2, the enzymes involved in the conversion of lactate into 1,2-propanediol are lactate CoA-transferase, lactoyl-CoA reductase and lactaldehyde reductase, the latter enzyme also being referred to as 1,2-propanediol oxidoreductase.

Preferably, activity of all enzymes according to the pathway of the invention, in particular of lactoyl-CoA reductase, lactate CoA-transferase and lactaldehyde reductase is chosen such that at least 100 mg propanediol per liter culture are produced.

In a second aspect, the present invention provides a host cell, preferably the host cell according to the main embodiment, wherein said host cell is engineered with one or more nucleic acids encoding (a) an enzyme having lactoyl-CoA reductase activity; and (b) (i) lactate CoA-transferase, and/or (ii) lactaldehyde reductase.

Embodiments falling under the second aspect include: A host cell, preferably the host cell of claim 1a, wherein said host cell is engineered with a nucleic acid encoding an enzyme having lactoyl-CoA reductase activity and a nucleic acid encoding lactate CoA-transferase; and a host cell, preferably the host cell of claim 1b, wherein said host cell is engineered with a nucleic acid encoding an enzyme having lactoyl-CoA reductase activity and a nucleic acid encoding lactaldehyde reductase.

This aspect provides specific means which render the host cell according to the invention an engineered or recombinant host cell. In particular, this embodiment requires that (a) nucleic acid(s) encoding the recited enzyme(s) has been introduced into the host cell. In other words, the host cell is, for example, transformed, transduced or transfected with such nucleic acid(s).

The enzymes required for engineering the pathway according to the present invention may be provided by (a) nucleic acid molecule(s) initially inserted in (a) vector(s) which can e.g. be synthesized by standard methods, or isolated from natural sources. Accordingly, provided are also one or more vectors, said vector(s) comprising nucleic acid(s) encoding the enzymes required by or recited in the main embodiment or embodiments described below.

Ligation of the coding sequences to transcriptional regulatory elements and/or to other amino acid encoding sequences comprised in the vector can be carried out using established methods. Transcriptional regulatory elements (parts of an expression cassette) ensuring expression in prokaryotes or eukaryotic cells are well known to those skilled in the art. These elements comprise regulatory sequences ensuring the initiation of transcription (e. g., translation initiation codon, promoters, such as naturally-associated or heterologous promoters and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers. Preferably, the polynucleotide(s) encoding the enzyme(s) of the invention is/are operatively linked to such expression control sequences allowing expression in prokaryotes or eukaryotic cells. The vector may further comprise nucleic acid sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the polynucleotide of the invention. Such leader sequences are well known in the art.

An expression cassette can be generated by fusing a suitable promoter with a suitable nucleotide sequence and a terminator signal or polyadenylation signal. The coding sequences can e.g. be synthesized by standard methods, or isolated from natural sources. For generating the expression cassette, customary recombination and cloning techniques are used as described, for example, by T. Maniatis, E. F. Fritsch and J. Sambrook, Molecular Cloning: A Laboratory Manual, Cold Spring Harbor Laboratory, Cold Spring Harbor, N.Y. (1989); by T. J. Silhavy, M. L. Berman and L. W. Enquist, Experiments with Gene Fusions, Cold Spring Harbor Laboratory, Cold Spring Harbor, N.Y. (1984) and by Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which allows optimal gene expression in said host. Vectors are well known to the skilled worker and can be found, for example, in "Cloning Vectors" (Pouwels P. H. et al., Ed., Elsevier, Amsterdam-N.Y.-Oxford, 1985). Vectors are to be understood as meaning not only plasmids, but all other vectors known to the skilled worker such as, for example, phages, viruses such as SV40, CMV, baculovirus and adenovirus, transposons, IS elements, phasmids, cosmids, and linear or circular DNA. These vectors can be replicated autonomously in the host organism or chromosomally.

Non-limiting examples of vectors include prokaryotic plasmid vectors, such as the pUC-series, pBluescript (Stratagene), the pET-series of expression vectors (Novagen) or pCRTOPO (Invitrogen) and vectors compatible with an expression in mammalian cells like pREP (Invitrogen), pcDNA3 (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for *Pichia pastoris* comprise e.g. the plasmids pAO815, pPIC9K and pPIC3.5K (all Invitrogen). Examples of plasmid vectors suitable for *C. glutamicum* comprise e.g. the *C. glutamicum/E. coli* shuttle vectors pEK-Ex1, pEC-XK99E, or pBL1 derivatives (pEK0).

Furthermore, it is preferred that the vector of the invention comprises a selectable marker. Examples of selectable markers include neomycin, gentamycin, ampicillin, zeocin, and hygromycin resistance and the like. Specifically-designed vectors allow the shuttling of DNA between different hosts, such as between bacteria and fungal cells or between bacteria and animal cells.

The vectors according to the invention allow the generation of recombinant host cells which are transformed, for example, with at least one vector comprising (a) sequence(s) encoding the enzymes required for the pathway according to the invention. It is preferred to use cloning and transfection methods known to the skilled worker, for example co-precipitation, protoplast fusion, electroporation, retroviral transfection and the like, in order to achieve expression of the above-mentioned nucleic acid(s) in the expression system in question. Suitable systems are described, for example, in Current Protocols in Molecular Biology, F. Ausubel et al., Ed., Wiley Interscience, New York 1997.

Alternatively, the nucleic acid(s) according to the above described second aspect is/are inserted into the suitable host cell's chromosome. Methods of stable chromosomal integration suitable for the respective host cell are known to persons skilled in the art. For example, genes can be integrated into the chromosome of the host cell in a targeted fashion by using a plasmid that does not replicate in the host cell.

In a further preferred embodiment, said enzyme having lactoyl-CoA reductase activity is optimized as compared to a naturally occurring enzyme having lactoyl-CoA reductase activity in that preferably said enzyme has improved lactoyl-CoA specificity, reduced side reaction activity, improved enzymatic activity, improved total turnover, and/or improved substrate affinity. Total turnover improvement can also be achieved through improved stability. All mentioned improvements can be achieved not only generally, but also specifically for desired reaction conditions. For instance, maintaining full activity at elevated reaction temperatures or changed pH values is an example of an improvement.

The proposed enzymatic conversion can further be optimized by choosing or developing a preferably highly active and/or highly specific lactate CoA-transferase, preferably characterized by one or more of the following properties: a high $k_{cat}$ for the reaction lactate+R-CoA<->lactoyl-CoA+R—OH, a low $K_m$ for lactate and R—CoA, and a strong specificity for lactate and R—CoA. A preferred CoA-donor is acetyl-CoA. The specificity should be strong for lactate as CoA-acceptor compared to other acids (pyruvate, acetate, propionate, butyrate, fumarate, succinate, malate, coumarate, fatty acids). In the case that a chosen host cell has further potential CoA-donor(s) besides acetyl-CoA, such as the ubiquitous citric acid cycle intermediate succinyl-CoA or the fatty acid biosynthesis intermediate malonyl-CoA, it can be advantageous to have a high specificity for one specific CoA-donor such as acetyl-CoA over the other CoA-donor(s).

In a further preferred embodiment of the host cell according to the first or second aspect of the invention, said host cell is capable of producing lactate.

As stated above, virtually all naturally occurring cells produce lactate or are capable of producing lactate, at least to a certain degree. Producers or high producers of lactate are either known (*lactobacilli, lactococci*) or can be selected by the skilled person, for example by monitoring the amount of lactate formed in a culture of a candidate host cell.

In a further preferred embodiment, the host cell is selected from a microorganism, a plant cell and an animal cell, preferably from the kingdom of bacteria, archea, yeast and fungi, more preferably from the genus of *Lactobacillus, Lactococcus, Clostridium, Escherichia, Pseudomonas, Bacillus, Saccharomyces, Pichia, Corynebacterium* and *Aspergillus*, yet more preferably *E. coli*.

In a further preferred embodiment, said enzyme with lactoyl-CoA reductase activity is selected from succinyl-CoA reductases, malonyl-CoA reductases, butyryl-CoA reductases, propionyl-CoA reductases and acetyl-CoA reductases. The present inventors recognized that these classes of enzymes are capable of providing lactoyl-CoA reductase activity.

In a further preferred embodiment, said nucleic acid encoding lactate CoA-transferase comprises or consists of the sequence of SEQ ID NO: 1 or a sequence encoding a protein with at least 40% amino acid sequence identity to the protein encoded by sequence of SEQ ID NO: 1; and/or said nucleic acid encoding lactoyl-CoA reductase comprises or consists of any of the sequences set forth in SEQ ID NOs: 2 to 5 or a sequence encoding a protein with at least 40% amino acid sequence identity to any one protein encoded by of SEQ ID NOs: 2 to 5; and/or said nucleic acid encoding lactaldehyde reductase comprises or consists of the sequence set forth in SEQ ID NO: 6 or a sequence encoding a protein with at least 40% amino acid sequence identity to the protein encoded by sequence of SEQ ID NO: 6.

The sequence of SEQ ID NO: 1 is that of the pct gene from *Clostridium propionicum* DSM1682. The sequence is identical to that of database entry AJ276553 in the GenBank database (version of Jun. 3, 2011). The indicated enzymatic activities are propionate CoA-transferase and lactate CoA-transferase; the corresponding EC numbers are EC 2.8.3.1 and EC 2.8.3.-.

The sequence of SEQ ID NO: 2 is that of the sucD gene from *Clostridium kluyveri* DSM555. The sequence is identical to that of database entry ID=5394466 in the GenBank database (version of June 3, 2011). The indicated enzymatic activity is succinyl-CoA reductase; the corresponding EC number is EC 1.2.1.76.

The sequence of SEQ ID NO: 3 is that of the Msed_0709 gene from *Metallosphaera sedula* DSM5348. The sequence is identical to that of database entry ID=5103747 in the GenBank database (version of June 3, 2011). The indicated enzymatic activities are succinyl-CoA reductase and malonyl-CoA reductase; the corresponding EC numbers are EC 1.2.1.76 and EC 1.2.1.75.

The sequence of SEQ ID NO: 4 is that of the mcr gene from *Sulfolobus tokodaii* strain 7 DSM16993. The sequence is identical to that of database entry ID=1460244 in the GenBank database (version of Jun. 3, 2011). The indicated enzymatic activity is malonyl-CoA reductase; the corresponding EC number is EC 1.2.1.75.

The sequence of SEQ ID NO: 5 is that of the pduP gene from *Salmonella enterica* Serovar *Typhimurium* LT2 DSM17058. The sequence is identical to that of database entry ID=1253572 in the GenBank database (version of June 3, 2011). The indicated enzymatic activity is propionyl-CoA reductase (propionaldehyde dehydrogenase); the corresponding EC number is EC 1.2.1.-.

The sequence of SEQ ID NO: 6 is that of the fucO gene from *Escherichia coli* K-12 substr. MG1655. The sequence is identical to that of database entry ID=947273 in the GenBank database (version of Jun. 3, 2011). The indicated enzymatic activity is lactaldehyde reductase (1,2-propanediol oxidoreductase); the corresponding EC number is EC 1.1.1.77.

Preferably, the above-mentioned sequence identity at the amino acid level is, independently for each sequence, at least 40%, at least 50%, at least 60%, at least 70%, at least 80%, at least 90%, at least 91%, at least 92%, at least 93%, at least 94%, at least 95%, at least 96%, at least 97%, at least 98%, or at least 99%.

It is understood that the recited nucleic acids, to the extent they exhibit less than 100% sequence identity to the specific SEQ ID NOs., exhibit the enzymatic activity of a protein encoded by the respective SEQ ID NO. Presence and absence of the respective enzymatic activity can be assayed by the skilled person using tests known in the art without further ado.

In a further preferred embodiment, said host cell has (a) an elevated expression or activity of glycerol kinase and/or glycerol-3-phosphate dehydrogenase, (b) a decreased expression or activity of fumarate reductase, and/or phosphate acetyltransferase, and/or alcohol/acetaldehyde dehydrogenase, (c) a decreased expression or activity of aerobic D-lactate dehydrogenase, (d) a decreased expression or activity of lactaldehyde dehydrogenase, (e) an elevated expression or activity of glycerol dehydrogenase and/or dihydroxyacetone kinase, (f) an elevated expression or activity of glycerol dehydrogenase with reduced lactaldehyde specificity and/or reduced expression or activity of the host's natural glycerol dehydrogenase, (g) a decreased expression or activity of pyruvate-formate lyase, (h) an elevated expression or activity of pyruvate decarboxylase; and/or (i) an elevated expression or activity of a glycerol importer.

Figure 3:
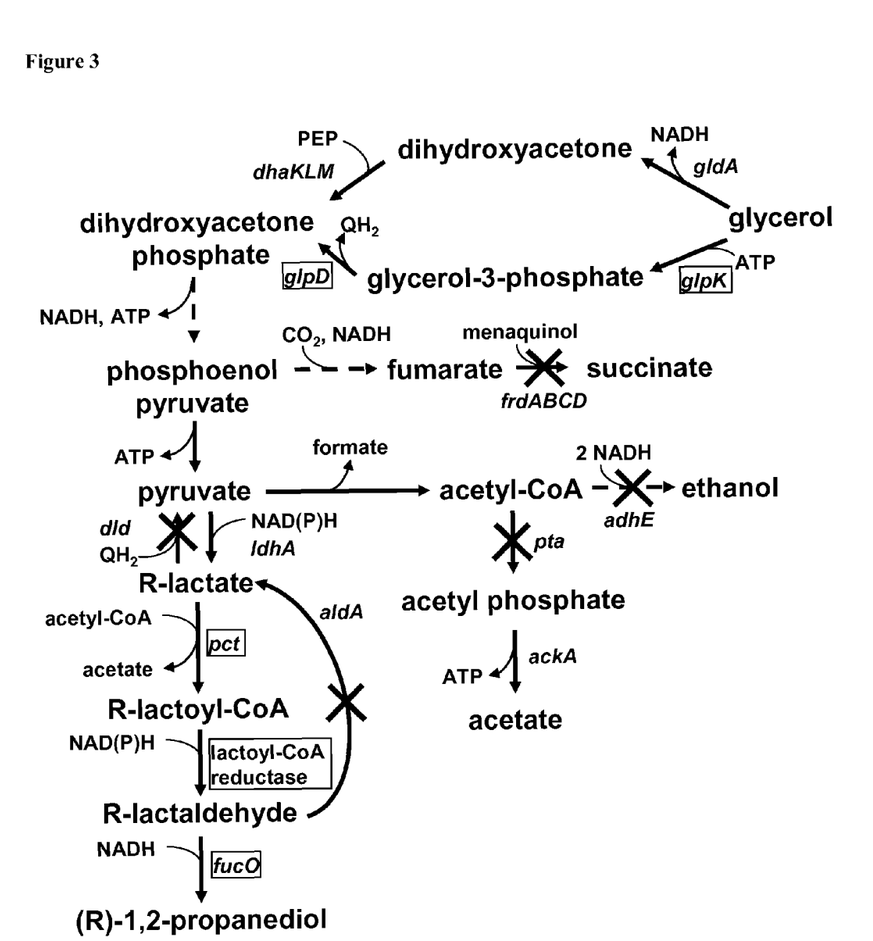
FIG. 3: An engineered *E. coli* pathway for the efficient production of 1,2-propanediol from glycerol. Crossed-out arrows depict host reactions eliminated through gene deletion. Boxed genes/functions depict overexpressed homologous or heterologous genes/functions.

This embodiment provides for a further optimization of the implementation of the pathway in the host cells according to the invention. To the extent this embodiment refers to elevated expression, the elevated expression or activity of the recited enzymes preferably serves to further enhance the carbon flux to lactate or lactoyl-CoA or precursors thereof as displayed further up in the pathway scheme as shown in FIGS. 2 and 3 as enclosed herewith. To the extent the present preferred embodiment refers to decreased expression or activity, it serves to reduce or turn off unwanted side reactions which side reactions would direct the carbon flux away from any of the mentioned precursors.

In a third aspect, the present invention provides a method of producing lactaldehyde and/or 1,2-propanediol, said method comprising (a) culturing (i) a host cell having elevated expression or activity of an enzyme having lactoyl-CoA reductase activity; (ii) a host cell being engineered with a nucleic acid encoding an enzyme having lactoyl-CoA reductase activity; or (iii) a host cell according to the invention; and/or (b) utilizing (i) an enzyme having lactoyl-CoA reductase activity as defined herein above, or (ii) the enzymes as defined herein above, to produce said compound.

Related thereto, the present invention provides in a fourth aspect the use of (a)(i) a host cell having elevated expression or activity of an enzyme having lactoyl-CoA reductase activity; (ii) a host cell being engineered with a nucleic acid encoding an enzyme having lactoyl-CoA reductase activity; or (iii) a host cell according to the invention; and/or of (b) (i) an enzyme having lactoyl-CoA reductase activity as defined herein above; or (ii) the enzymes as defined in relation to first and second aspect, for the production of lactaldehyde and/or 1,2-propanediol.

These two aspects provide for the production of lactaldehyde and/or 1,2-propanediol and may use either a host cell, according to the invention, or, in the alternative, the enzymes recited above. To explain further, the latter alternative preferably relates to a cell free system comprising one or more of the recited enzymes. For example, if lactate is provided and lactaldehyde is to be produced, the required enzymes are lactate CoA-transferase and lactoyl-CoA reductase. In a further example, and assuming that lactoyl-CoA is provided and 1,2-propanediol is to be produced, lactoyl-CoA reductase and lactaldehyde reductase are the required enzymes. Moreover, these aspects of the invention envisage furthermore the use of an enzyme having lactoyl-CoA reductase activity. As stated above, the present inventors recognized that enzymes known as such, for example succinyl-CoA reductases, malonyl-CoA reductases, butyryl-CoA reductases, propionyl-CoA reductases and acetyl-CoA reductases, can be used to provide lactoyl-CoA reductase activity. Similarly, not only the above disclosed host cells according to the invention may be employed in method and use according to third and fourth aspect of the invention, but also a host cell as defined in items (a)(i) and (a)(ii) of both third and fourth aspect, noting that the prior art fails to suggest use of the latter type of host cell for the purposes according to the present invention.

The host cell can be cultured and fermented by known methods. Bacteria can, for example, be multiplied in TB or LB medium at a temperature of 20 to 40° C., preferably 25 to 35° C., and more preferred at 30° C., and a pH of 6 to 9.

Preferred pH-values are 7 and 8. Suitable culture conditions are described in detail for example by T. Maniatis, E. F. Fritsch and J. Sambrook, Molecular Cloning: A Laboratory Manual, Cold Spring Harbor Laboratory, Cold Spring Harbor, N.Y. (1989). Appropriate culture mediums and conditions for the above-described host cells are well known in the art.

In a preferred embodiment of the method according to the third aspect and the use according to the fourth aspect of the invention, sugar, fat, lipid, wax, alcohol such as glycerol, protein and/or carbon dioxide is/are used as carbon source(s). Accordingly, a preferred substrate for the invented enzymatic process, lactate, can be derived by biosynthesis from numerous carbon sources known to be degradable by microorganisms, such as sugar, fatt, lipids, wax, alcohol, glycerol, protein, carbon dioxide or others. Lactate is a major natural fermentation product, even determining the nomenclature of bacterial families like *Lactococcus* or *Lactobacillus* species. Thus, strong natural producers of lactate are known, but can also be engineered from common hosts like *E. coli* (Mazumdar et al., AEM 2010, 76(13): 4327-4336).

The enzymatic reduction of lactate to lactaldehyde via lactoyl-CoA gives rise to the biotechnological utilization of the efficient carbon stream towards lactate for the synthesis of desired products such as lactaldehyde or PD. As disclosed above, a recombinant organism and a method are provided to produce PD from various carbon sources through a non-natural biosynthetic pathway utilizing the enzyme(s) according to the invention and via the intermediate lactoyl-CoA. To this end, for example, a lactate producing strain is transformed with a plasmid containing genes encoding lactate CoA-transferase, lactoyl-CoA reductase and a lactaldehyde reductase (1,2-propanediol oxidoreductase) under the control of a constitutive promoter. Further improvements can be made through metabolic engineering towards increased availability of lactate as an intermediate, acetyl-CoA for the transferase activity, and reducing equivalents (NADH) for the reduction to PD, i.e. through elimination of other NAD(P)H consuming fermentation pathways, for example as discussed above.

The present invention further, in a fifth aspect, provides a kit comprising or consisting of (a) an enzyme with lactoyl-CoA reductase activity; and (b) (i) lactate CoA-transferase; and/or (ii) lactaldehyde reductase; and/or one or more nucleic acids encoding said enzymes according to (a) and (b).

In a preferred embodiment, the enzymes comprised in said kit or encoded by the nucleic acid(s) comprised in said kit are those which are subject of preferred embodiments of the host cell according to the invention. In particular, it is preferred that said enzyme with lactoyl-CoA reductase activity is selected from succinyl-CoA reductases, malonyl-CoA reductases, butyryl-CoA reductases, propionyl-CoA reductases and acetyl-CoA reductases. Furthermore, it is preferred that (a) said nucleic acid encoding lactate CoA-transferase comprises or consists of the sequence of SEQ ID NO: 1 or a sequence encoding a protein with at least 40% amino acid sequence identity to the protein encoded by sequence of SEQ ID NO: 1; and/or (b) said nucleic acid encoding lactoyl-CoA reductase comprises or consists of any of the sequences set forth in SEQ ID NOs: 2 to 5 or a sequence encoding a protein with at least 40% amino acid sequence identity to any protein encoded by sequences of SEQ ID NOs: 2 to 5; and/or (c) said nucleic acid encoding lactaldehyde reductase comprises or consists of the sequence of SEQ ID NO: 6 or a sequence encoding a protein with at least 40% amino acid sequence identity to the protein encoded by sequence of SEQ ID NO: 6.

In preferred embodiments according to the invention the kits, to the extent they comprise nucleic acids, comprise only the specifically recited nucleic acids. In other words, while non-nucleic acid components may be present, it is preferred that no other nucleic acid acid(s) than the recited one(s) is/are present.

The present invention, in a sixth aspect, provides the use of an enzyme selected from succinyl-CoA reductases, malonyl-CoA reductases, butyryl-CoA reductases, propionyl-CoA reductases and acetyl-CoA reductases for providing lactoyl-CoA reductase activity. As stated above, the present inventors surprisingly found out that these enzyme classes may be used to provide, in addition to the known activities for each enzyme, lactoyl-CoA reductase activity which is a key activity for implementing the pathway according to the present invention.

EXAMPLES

The examples illustrate the invention but is not to be construed as being limiting:

Example 1

Experimental Proof for a Lactoyl-CoA Reductase

Three enzymatic reactions define key aspects of the present invention, lactoyl-CoA transferase, lactoyl-CoA reductase and lactaldehyde reductase. Two of these reactions and appropriate enzymes are well known and have been shown to function well for the purpose intended in this invention: lactoyl-CoA transferase/propionyl-CoA transferase encoded by the *Clostridium propionicum* gene pct has been shown to transfer coenzyme A to lactate and to use various donors, such as propionyl-CoA or acetyl-CoA (Schweiger, Buckel, FEBS Lett. 171 (1984), 79-84). The lactaldehyde reductase/1,2-propanediol oxidoreductase encoded by the *E. coli* gene fucO has been shown to reduce lactaldehyde to 1,2-propanediol (Boronat, Aguilar, J Bacteriol. 140 (1979), 320-326). The key reaction of this invention, a reduction of lactoyl-CoA, has never been described or observed. Here we demonstrate such activity, monitored by NADH cofactor consumption by a cell extract in the presence of the substrate lactoyl-CoA.

The substrate lactoyl-CoA was synthesized from lactate, coenzyme A and ATP with the enzyme acetyl-coenzyme A synthetase from *Saccharomyces cerevisiae* (EC 6.5.1.1), according to Freckel and Kitchen (J. Biol. Chem. 252 (1977), 504-507). Successful synthesis was verified by HPLC-MS (data not shown).

Figure 4:
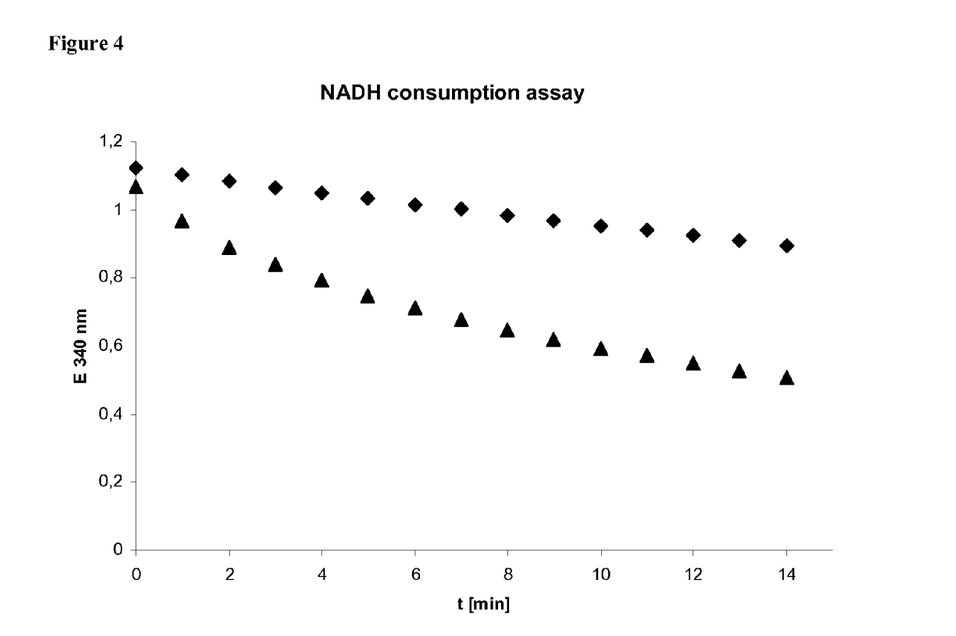
FIG. 4: Diagram of NADH consumption assays with cell extract possessing lactoyl-CoA reductase activity in the presence (triangles) or absence (diamonds) of the substrate lactoyl-CoA.

In a NADH consumption assay, 25 mM Tris-HCl pH=7.5 buffer, with 1 mM DTT, 0.3 mM NADH and 10% (v/v) cell extract possessing lactoyl-CoA reductase activity was pre-incubated at room temperature. After 5 min, the assay was started with the addition of 0.2 mM lactoyl-CoA and the reduction of lactoyl-CoA with accompanying oxidation of NADH to NAD$^+$ was photometrically monitored at 340 nm. Significant NADH consumption was only observed in reactions with a cell extract possessing lactoyl-CoA reductase activity and the substrate lactoyl-CoA (FIG. 4, triangles). Negative controls without lactoyl-CoA (FIG. 4, diamonds) or without cell extract possessing lactoyl-CoA reductase activity or with cell extract possessing no lactoyl-CoA reductase activity (data not shown) instead showed only low NADH consumption (background activity).

Example 2

Optimization

One or more of the following modifications may be made for a yet further efficient production as compared to the embodiments disclosed above of PD from glycerol in *E. coli* utilizing the lactate to lactaldehyde reduction according to the present invention; see also FIG. 3.

Deletion of fumarate reductase (ΔfrdA), phosphate acetyltransferase (Δpta), and alcohol/acetaldehyde dehydrogenase (ΔadhE) to reduce fermentation routes competing for NADH; deletion of aerobic D-lactate dehydrogenase (Δdld) to prevent degradation of lactate to pyruvate and deletion of lactaldehyde dehydrogenase (ΔaldA) to prevent degradation of lactaldehyde back to lactate; overexpression of homologous glpK and glpD for increased convertion of glycerol to the intermediate dihydroxyacetone phosphate under micro-aerob conditions; overexpression of lactate CoA-transferase (such as pct gene from *C. propionicum* DSM1682), a lactoyl-CoA reductase according to the present invention and a homologous 1,2-propanediol oxidoreductase (fucO) for the final, determining steps of the PD biosynthetic pathway according to the present invention.

The recombinant host can further be optimized through one or more of the following modifications:

overexpression of glycerol dehydratase (gldA) and dihydroxyacetone kinase (dhaKLM) for increased glycerol degradation under anaerob or micro-aerob conditions; replacement of the host intrinsic (homologous) phosphoenol pyruvate utilizing dihydroxyacetone kinase activity, achieved by deletion of dhaKLM and recombinant expression of dhaK from *Citrobacter freundii* DSM30040, encoding an ATP utilizing single-protein dihydroxyacetone kinase. To maintain provision of acetyl-CoA and increase NADH availability, pyruvate-formate lyase activity (plB) can be reduced and pyruvate decarboxylase activity (aceE+aceF+lpd) increased through overexpression of a NADH insensitive lipoamide dehydrogenase subunit (for example mutated lpd*, see Kim et al., J. Bacteriol. 2008, 190: 3851-3858); overexpression of the glycerol importer (glpF) to enhance glycerol uptake.

The invention claimed is:

1. A host cell engineered with one or more nucleic acids encoding
   (a) an enzyme having lactoyl CoA-reductase activity, wherein said enzyme with lactoyl-CoA reductase activity is selected from succinyl-CoA reductases, malonyl-CoA reductases, butyryl-CoA reductases, propionyl-CoA reductases and acetyl-CoA reductases; and
   (b) lactaldehyde reductase;
   wherein said engineered host cell has an elevated expression or activity of the enzymes encoded by said nucleic acids, as compared with the parent cell from which it has been derived.

2. The host cell according to claim 1, wherein
   (a) said nucleic acid encoding lactoyl-CoA reductase comprises the sequence of SEQ ID NO: 2, and
   (b) said nucleic acid encoding lactaldehyde reductase comprises the sequence of SEQ ID NO: 6.

3. A kit comprising
   (a) an enzyme with lactoyl-CoA reductase activity, wherein said enzyme with lactoyl-CoA reductase activity is selected from succinyl-CoA reductases, malonyl-CoA reductases, butyryl-CoA reductases, propionyl-CoA reductases and acetyl-CoA reductases; and
   (b) lactaldehyde reductase;
   or one or more nucleic acids encoding said enzymes according to (a) and (b).

4. The kit according to claim 3, wherein said enzyme with lactoyl-CoA reductase activity is selected from succinyl-CoA reductases.

5. The kit according to claim 4, wherein the succinyl-CoA reductase is encoded by the sequence of SEQ ID NO. 2, and wherein the lactaldehyde reductase is encoded by the sequence of SEQ ID NO. 6.

* * * * *

SEQUENCE LISTING

```
<160> NUMBER OF SEQ ID NOS: 6

<210> SEQ ID NO 1
<211> LENGTH: 1575
<212> TYPE: DNA
<213> ORGANISM: Clostridium propionicum DSM1682

<400> SEQUENCE: 1
atgagaaagg ttcccattat taccgcagat gaggctgcaa agcttattaa agacggtgat        60
acagttacaa caagtggttt cgttggaaat gcaatccctg aggctcttga tagagctgta       120
gaaaaaagat tcttagaaac aggcgaaccc aaaaacatta catatgttta ttgtggttct       180
caaggtaaca gagacggaag aggtgctgag cactttgctc atgaaggcct tttaaaacgt       240
tacatcgctg tcactgggc tacagttcct gctttgggta aaatggctat ggaaaataaa       300
atggaagcat ataatgtatc tcagggtgca ttgtgtcatt tgttccgtga tatagcttct       360
cataagccag gcgtatttac aaaggtaggt atcggtactt tcattgaccc cagaaatggc       420
ggcggtaaag taaatgatat taccaaagaa gatattgttg aattggtaga gattaagggt       480
caggaatatt tattctaccc tgcttttcct attcatgtag ctcttattcg tggtacttac       540
gctgatgaaa gcggaaatat cacatttgag aaagaagttg ctcctctgga aggaacttca       600
gtatgccagg ctgttaaaaa cagtggcggt atcgttgtag ttcaggttga aagagtagta       660
aaagctggta ctcttgaccc tcgtcatgta aaagttccag gaatttatgt tgactatgtt       720
gttgttgctg acccagaaga tcatcagcaa tctttagatt gtgaatatga tcctgcatta       780
tcaggcgagc atagaagacc tgaagttgtt ggagaaccac ttcctttgag tgcaaagaaa       840
gttattggtc gtcgtggtgc cattgaatta gaaaaagatg ttgctgtaaa tttaggtgtt       900
ggtgcgcctg aatatgtagc aagtgttgct gatgaagaag gtatcgttga ttttatgact       960
ttaactgctg aaagtgtggt gtattggtggt gttcctgctg gtggcgttcg ctttggtgct      1020
```

```
tcttataatg cggatgcatt gatcgatcaa ggttatcaat tcgattacta tgatggcggc    1080
ggcttagacc tttgctattt aggcttagct gaatgcgatg aaaaaggcaa tatcaacgtt    1140
tcaagatttg gccctcgtat cgctggttgt ggtggtttca tcaacattac acagaataca    1200
cctaaggtat tcttctgtgg tactttcaca gcaggtggct taaggttaa aattgaagat     1260 ggcaaggtta ttattgttca agaaggcaag cagaaaaaat tcttgaaagc tgttgagcag    1320
attacattca atggtgacgt tgcacttgct aataagcaac aagtaactta tattacagaa    1380
agatgcgtat tccttttgaa ggaagatggt ttgcacttat ctgaaattgc acctggtatt    1440
gatttgcaga cacagattct tgacgttatg gattttgcac ctattattga cagagatgca    1500
aacggccaaa tcaaattgat ggacgctgct ttgtttgcag aaggcttaat gggtctgaag    1560
gaaatgaagt cctga                                                     1575
```

<210> SEQ ID NO 2
<211> LENGTH: 1362
<212> TYPE: DNA
<213> ORGANISM: Clostridium kluyveri DSM555

<400> SEQUENCE: 2

```
atgagtaatg aagtatctat aaaagaatta attgaaaagg caaggtggc acaaaaaaaa     60 ttggaagcct atagtcaaga acaagttgat gtactagtaa aagcactagg aaaagtggtt    120
tatgataatg cagaaatgtt tgcaaaagaa gcagttgaag aaacagaaat gggtgtttat    180
gaagataaag tagctaaatg tcatttgaaa tcaggagcta tttggaatca tataaaagac    240
aagaaaactg taggcataat aaaagaagaa cctgaaaggg cacttgttta tgttgctaag    300
ccaaagggag ttgtggcagc tactacgcct ataactaatc cagtggtaac tcctatgtgt    360
aatgcaatgg ctgctataaa gggcagaaat acaataatag tagcaccaca tcctaaagca    420
aagaaagttt cagctcatac tgtagaactt atgaatgctg agcttaaaaa attgggagca    480
ccagaaaata tcatacagat agtagaagca ccatcaagag aagctgctaa ggaacttatg    540
gaaagtgctg atgtagttat tgctacaggc ggtgctggaa gagttaaagc tgcttactcc    600
agtggaagac cagcttatgg cgttggacct ggaaattcac aggtaatagt tgataaggga    660
tacgattata taaaagctgc acaggatata ataacaggaa gaaatatga caatggaatt    720 atatgttctt cagagcaatc agttatagct cctgctgaag attatgataa ggtaatagca    780
gcttttgtag aaaatggggc attctatgta gaagatgagg aaacagtaga aaagtttaga    840 tcaacttat ttaaagatgg aaaaataaac agcaagatta taggtaaatc cgtccaaatt     900
attgcggatc ttgcaggagt aaaagtacca gaaggtacta aggttatagt acttaagggt    960
aaaggtgcag agaaaaaga tgtactttgt aaagaaaaa tgtgtccagt tttagtagca    1020
ttgaaatatg atactttga agaagcagtt gaaatagcta tggctaatta tatgtatgaa    1080
ggagctggtc atacagcagg catacattct gacaatgacg agaacataag atatgcagga    1140
actgtattac ctataagcag attagttgta aatcagcctg caactactgc tggaggaagt    1200
ttcaataatg gatttaaccc tactactaca ctaggctgcg gatcatgggg cagaaacagt    1260
atttcagaaa atcttactta cgagcatctt ataaatgttt caagaatagg gtatttcaat    1320
aaagaagcaa aagttcctag ctatgaggaa atatgggat aa                        1362
```

<210> SEQ ID NO 3
<211> LENGTH: 1074
<212> TYPE: DNA

<213> ORGANISM: Metallosphaera sedula DSM5348

<400> SEQUENCE: 3

```
atgaggagaa cgctaaaggc cgcaattctc ggggccacag gtctggttgg aatagaatac      60
gtgagaatgt tagctgatca tccctacatc aagccaacat atcttgcagg aaagggttcc     120
gtgggaaagc cctatggcga atagttaga tggcaaacag ttgggaacgt gcccaaagag      180
gtagccaacc aagaggtaaa accaacggat ccgaagctaa tggatgacgt tgacataatt     240
ttctctccgc taccgcaggg cgcagcggga cctgtcgagg agcagttcgc aaagctaggc     300
ttcaacgtga tcagcaattc tccggatcac aggtttgata tggacgttcc catgataata     360
ccggaggtca atccgcatac cgtgaccta attgacgagc aaaggaagag gagggactgg     420
aagggattca tagttaccac tcccttatgc acggcccagg gagctgcaat cccctaacg     480
cccatttatc agaacttcaa gatgagcggt gtaatgataa ccacaatgca atccttgtca     540
ggtgctggct atccgggaat cgcttccctg gatattgtgg acaacgctct ccccctggga     600
gatgggtacg acgccaagac cgtgaaggag ataacaagaa tactatcaga ggttaagagg     660
aacgttcagg agcccggcgt caacgagata accctggatg ctactaccca tagaattgca     720
acaattcacg gtcactacga ggtagcatac gtaaccttca aggaggacac agacgttaga     780
aaggtaatgg agtcgatgga gtccttcaag ggagaacccc aggacctgaa gttaccaaca     840
gcaccagaga agccaatcat agttacgaca caggacgcta gaccacaggt attcttcgat     900
aggtgggctg gaaatccgcc cggaatgagc gttgttgtgg aaggctaaa gcaggttaac      960
ccaaggacca taaggttcgt ttcgctaatc cataacacag ttagggggagc agctggaggc    1020
ggtgtgctga cagctgagct cttagtggag aagggctaca tagacaagag atga          1074
```

<210> SEQ ID NO 4
<211> LENGTH: 1080
<212> TYPE: DNA
<213> ORGANISM: Sulfolobus tokodaii strain 7 DSM16993

<400> SEQUENCE: 4

```
gtgatactca tgaggagaac attaaaagcc gcaatattag gtgctactgg tttagtagga      60
atcgaatacg taagaatgct atcaaatcat ccttatatta aaccagcata tttagctgga     120
aaaggttcag tgggtaaacc gtatggtgag gtagtaagat ggcaaacagt aggacaagtt     180
cctaaggaaa tagctgatat ggaaataaaa ccaactgatc ctaagttaat ggatgatgta     240
gacataaatt tttctccatt acctcaaggt gctgctggcc cagtagaaga acaatttgca     300
aaagaaggat tccctgtgat tagtaattca ccagatcata gatttgatcc tgatgttccc     360
ttattggttc ctgaactaaa tcctcatact attagcttaa ttgatgagca agaaaaaga     420
agagaatgga aaggatttat agtaactaca ccactatgca cagcccaggg tgcagcaata     480
ccattaggtg ctatatttaa agattataag atggatggag catttataac tactattcaa     540
tcgctatctg gtgccggtta tccaggaata ccatcattag atgtagtaga taatatcttg     600
cctttaggtg atggatacga tgccaagacg ataaaagaga tcttcagaat tttaagcgaa     660
gttaagagaa atgtagatga acctaaatta gaagatgtaa gcttagcagc aacaactcat     720
agaatagcta ctatacatgg tcattatgaa gtactatatg tatcgttcaa agaggaaact     780
gctgctgaaa agttaaggga gactttagaa aactttagag gggaaccaca agatctaaaa     840
ttaccaactg caccttcaaa gccaattatc gttatgaatg aggatacaag acctcaagtc     900
tattttgata gatgggctgg ggatattcca ggaatgagtg tagttgtagg tagattaaag     960
```

```
caagtgaata agagaatgat aaggttagta tcattaattc ataacacggt cagaggagcc    1020
gcaggaggag gtatattagc agctgaatta cttgtcgaaa aaggatatat tgaaaagtaa    1080
```

<210> SEQ ID NO 5
<211> LENGTH: 1395
<212> TYPE: DNA
<213> ORGANISM: Salmonella enterica Serovar Typhimurium LT2 DSM17058

<400> SEQUENCE: 5

```
atgaatactt ctgaactcga aaccctgatt cgcaccattc ttagcgagca attaaccacg      60
ccggcgcaaa cgccggtcca gcctcagggc aaagggattt tccagtccgt gagcgaggcc     120
atcgacgccg cgcaccaggc gttcttacgt tatcagcagt gcccgctaaa aacccgcagc     180
gccattatca gcgcgatgcg tcaggagctg acgccgctgc tggcgcccct ggcggaagag     240
agcgccaatg aaacggggat gggcaacaaa gaagataaat ttctcaaaaa caaggctgcg     300
ctggacaaca cgccgggcgt agaagatctc accaccaccg cgctgaccgg cgacggcggc     360
atggtgctgt ttgaatactc accgtttggc gttatcggtt cggtcgcccc aagcaccaac     420
ccgacggaaa ccatcatcaa caacagtatc agcatgctgg cggcgggcaa cagtatctac     480
tttagcccgc atccgggagc gaaaaaggtc tctctgaagc tgattagcct gattgaagag     540
attgccttcc gctgctgcgg catccgcaat ctggtggtga ccgtggcgga acccaccttc     600
gaagcgaccc agcagatgat ggcccacccg cgaatcgcag tactggccat taccggcggc     660
ccgggcattg tggcaatggg catgaagagc ggtaagaagg tgattggcgc tggcgcgggt     720
aacccgccct gcatcgttga tgaaacggcg gacctggtga agcggcgga agatatcatc     780 aacggcgcgt cattcgatta caacctgccc tgcattgccg agaagagcct gatcgtagtg     840
gagagtgtcg ccgaacgtct ggtgcagcaa atgcaaaacct tcggcgcgct gctgttaagc     900
cctgccgata ccgacaaact ccgcgccgtc tgcctgcctg aaggccaggc gaataaaaaa     960
ctggtcggca agagcccatc ggccatgctg gaagccgccg ggatcgctgt ccctgcaaaa    1020
gcgccgcgtc tgctgattgc gctggttaac gctgacgatc cgtgggtcac cagcgaacag    1080
ttgatgccga tgctgccagt ggtaaaagtc agcgatttcg atagcgcgct ggcgctggcc    1140
ctgaaggttg aagaggggct gcatcatacc gccattatgc actcgcagaa cgtgtcacgc    1200
ctgaacctcg cggcccgcac gctgcaaacc tcgatattcg tcaaaaacgg cccctcttat    1260
gccgggatcg cgtcggcgg cgaaggcttt accaccttca ctatcgccac accaaccggt    1320
gaagggacca cgtcagcgcg tactttgcc cgttcccggc gctgcgtact gaccaacggc    1380 tttctctattc gctaa                                                    1395
```

<210> SEQ ID NO 6
<211> LENGTH: 1152
<212> TYPE: DNA
<213> ORGANISM: Escherichia coli K-12 substr. MG1655

<400> SEQUENCE: 6

```
atgatggcta acagaatgat tctgaacgaa acggcatggt ttggtcgggg tgctgttggg      60
gctttaaccg atgaggtgaa acgccgtggt tatcagaagg cgctgatcgt caccgataaa     120
acgctggtgc aatgcggcgt ggtggcgaaa gtgaccgata gatggatgc tgcagggctg     180 gcatgggcga tttacgacgg cgtagtgccc aacccaacaa ttactgtcgt caaagaaggg     240
ctcggtgtat tccagaatag cggcgcggat tacctgatcg ctattggtgg tggttctcca     300
```

```
caggatactt gtaaagcgat tggcattatc agcaacaacc cggagtttgc cgatgtgcgt      360
agcctggaag ggctttcccc gaccaataaa cccagtgtac cgattctggc aattcctacc      420
acagcaggta ctgcggcaga agtgaccatt aactacgtga tcactgacga agagaaacgg      480
cgcaagtttg tttgcgttga tccgcatgat atcccgcagg tggcgtttat tgacgctgac      540
atgatggatg gtatgcctcc agcgctgaaa gctgcgacgg gtgtcgatgc gctcactcat      600
gctattgagg ggtatattac ccgtggcgcg tgggcgctaa ccgatgcact gcacattaaa      660
gcgattgaaa tcattgctgg ggcgctgcga ggatcggttg ctggtgataa ggatgccgga      720
gaagaaatgg cgctcgggca gtatgttgcg ggtatgggct tctcgaatgt tgggttaggg      780
ttggtgcatg gtatggcgca tccactgggc gcgtttata acactccaca cggtgttgcg      840
aacgccatcc tgttaccgca tgtcatgcgt tataacgctg actttaccgg tgagaagtac      900
cgcgatatcg cgcgcgttat gggcgtgaaa gtggaaggta tgagcctgga agaggcgcgt      960
aatgccgctg ttgaagcggt gtttgctctc aaccgtgatg tcggtattcc gccacatttg     1020
cgtgatgttg gtgtacgcaa ggaagacatt ccggcactgg cgcaggcggc actggatgat     1080
gtttgtaccg gtggcaaccc gcgtgaagca acgcttgagg atattgtaga gctttaccat     1140
accgcctggt aa                                                         1152
```